United States Patent [19]
Zampini et al.

[11] Patent Number: 5,618,932
[45] Date of Patent: Apr. 8, 1997

[54] PHOTOACTIVE COMPOUNDS AND COMPOSITIONS

[75] Inventors: Anthony Zampini, Westborough; Ashish Pandya, Natick, both of Mass.

[73] Assignee: Shipley Company, L.L.C., Marlborough, Mass.

[21] Appl. No.: 449,334

[22] Filed: May 24, 1995

[51] Int. Cl.⁶ .................. C07C 245/12; C07D 307/36; C07D 333/10; C07D 333/28
[52] U.S. Cl. .................. 534/557; 549/78; 549/502
[58] Field of Search .................. 534/557; 549/78, 549/502

[56] References Cited

U.S. PATENT DOCUMENTS

| | | | |
|---|---|---|---|
| 2,515,908 | 7/1950 | Stevens et al. | 549/502 X |
| 2,959,595 | 11/1960 | Beaver et al. | 549/78 |
| 3,046,118 | 7/1962 | Schmidt | 534/557 X |
| 3,489,815 | 1/1970 | Kraus, Jr. | 549/78 |
| 3,579,538 | 5/1971 | Meyer et al. | 549/78 |
| 4,222,883 | 9/1980 | Clinton | 549/502 X |
| 4,517,275 | 5/1985 | Stahlhofen | 534/557 X |
| 5,424,167 | 6/1995 | Uetani et al. | 430/191 |
| 5,514,515 | 5/1996 | Zampini et al. | 534/557 X |

FOREIGN PATENT DOCUMENTS

| | | |
|---|---|---|
| 0415266A2 | 3/1991 | European Pat. Off. . |
| 0430477A1 | 6/1991 | European Pat. Off. . |
| 0510672A1 | 10/1992 | European Pat. Off. . |
| 3616599 | 11/1987 | Germany . |
| 3616598 | 11/1987 | Germany . |
| 935250 | 1/1960 | United Kingdom . |
| 93/18438 | 9/1993 | WIPO . |

OTHER PUBLICATIONS

Foo et al., Chemical Abstracts, 102:205644 (1985).
Meyr et al., Chemical Abstracts; 72:90270 (1970).
Naarmann et al., Chemical Abstracts, 108;168129 (1988).

*Primary Examiner*—Fiona T. Powers
*Attorney, Agent, or Firm*—Robert L. Goldberg

[57] ABSTRACT

A new photoactive compound for use in the formulation of a photoresist comprises a bisphenol compound having an alkyl linkage substituted with a heterocyclic group. The new photoactive compound may be admixed with an alkali soluble resin to formulate a photoresist composition. The new photoactive compounds exhibit enhanced long term solubility in conventional photoresist solvents.

15 Claims, No Drawings

PHOTOACTIVE COMPOUNDS AND COMPOSITIONS

BACKGROUND OF THE INVENTION

1. Field of the Invention

The invention relates to phenolic polynuclear compositions useful as intermediates for the formation of photoactive compounds. Further, the invention relates to such photoactive compounds formed by the esterification of these phenolic compositions with sulfonyl halides of naphthoquinone diazide.

2. Description of the Background Art

Photoresists are photosensitive films used for transfer of an image to a substrate. They may be negative or positive acting. After a coating of a photoresist is formed on a substrate, the coating is selectively exposed through a photomask to a source of activating energy such as ultraviolet light. The photomask has areas that are opaque to activating radiation and other areas that are transparent to activating radiation. The pattern in the photomask of opaque and transparent areas define a desired image to be transferred to a substrate. A relief image is provided upon development of the latent image patterned in the resist coating. The background and use of photoresists are generally described, for example, in Deforest, *Photoresist Materials and Processes,* McGraw Hill Book Company, New York (1975), and by Moreau, *Semiconductor Lithography, Principles, Practices and Materials,* Plenum Press, New York (1988).

Various attempts have been made to alter the make-up of photoresist compositions to improve performance or functional properties. In particular, a variety of photoactive compounds have been reported including photoactive compounds that contain more than one diazoquinone moiety. It has been found, however, that many of such prior photoactive compounds exhibit undesirable properties and hence can be unsuitable for use in many resist formulations. For example, it has been reported that photoactive compounds having multiple photoactive groups exhibit poor solubility in typical photoresist solvents, limiting the shelflife of a resist containing such photoactive compounds. See, e.g., European Published Patent Application 0126266A2, incorporated herein by reference.

It thus would be desirable to have new polynuclear compounds and new photoactive compositions for use in photoresists. It would be further desirable to have new photoactive compounds that exhibit enhanced solubility in photoresist solvents and formulations.

SUMMARY OF THE INVENTION

The present invention is directed to compounds conforming to formula:

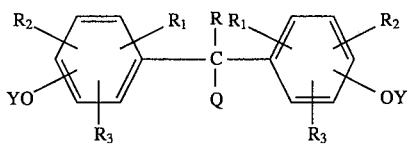

and more preferably, to the following formula:

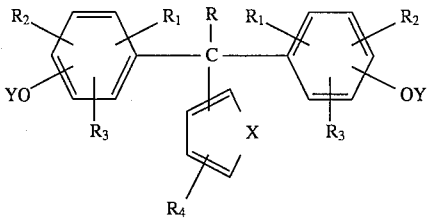

where in each of the above formulae, as applicable, Q is a five membered heterocylic group, Y group is independently selected from the group consisting of hydrogen, alkyl, $R'SO_2$, acyl, $(R')_3Si$ and naphthoquinone diazide sulfonyl (where each R' is independently substituted or unsubstituted alkyl having from 1 to 5 carbon atoms or substituted or unsubstituted aryl such as phenyl), with the proviso that in order for the compound to be a light sensitive compound, at least one of the said Y groups is naphthoquinone diazide sulfonyl, X is oxygen or sulfur; R is hydrogen, alkyl having from 1 to 5 carbon atoms, cyclic alkyl having from 3 to 6 carbon atoms, phenyl, substituted phenyl, saturated and aromatic heterocyclic; $R_1$ through $R_3$ are each independently selected from the group consisting of hydrogen, hydroxyl, substituted and unsubstituted alkyl having from 1 to 5 carbon atoms, cyclic alkyl having three to six carbon atoms, substituted and unsubstituted phenyl, substituted and unsubstituted alkoxy, substituted and unsubstituted alkenyl, substituted and unsubstituted alkynyl, nitro, alkanoyl, carboxyl, sulfonyl and halogen such as fluoro, chloro, bromo or iodo, $R_4$ is selected from a group consisting of hydrogen, substituted and unsubstituted alkyl having from 1 to 5 carbon atoms, substituted and unsubstituted alkoxy, substituted and unsubstituted alkenyl, substituted and unsubstituted alkynyl, carboxylic, alkoxy carbonyl, nitro, and halogen such as fluoro, chloro, bromo or iodo. When X is oxygen it is preferred that R4 is on the five position of the heterocyclic ring.

Preferably one or more of the $R_1$ through $R_3$ groups of compounds of formula I are hydroxyl ring substituents, more preferably one or two of the $R_1$ through $R_3$ groups are hydroxyl ring substituent and still more preferably one of the $R_1$ through $R_3$ groups is a hydroxyl ring substituent.

Suitable naphthoquinone diazide sulfonyl group(s) for formation of photoactive compounds of formula I include a 1,2-naphthoquinonediazide-4-sulfonyl group, a 1,2-naphthoquinonediazide-5-sulfonyl group, a 2,1-naphthoquinonediazide-4-sulfonyl group, a 2,1-naphthoquinonediazide-6-sulfonyl group, a 2,1-naphthoquinonediazide-7-sulfonyl group, and a 2,1-naphthoquinonediazide-8-sulfonyl group. These groups may be used alone or in combination as a mixture. Among these groups, a 1,2-naphthoquinonediazide-4-sulfonyl group and a 1,2-naphthoquinonediazide-5-sulfonyl group are particularly preferred.

Preferred photoactive compounds of formula I exhibit high and prolonged solubility in typical photoresist solvents. Particularly preferred are those photoactive polynuclear compounds of the invention that remain dissolved (no precipitation detected by optical microscope) in a photoresist solvent system (single solvent or mixture) at a concentration of five weight percent for 90 or more days.

The compounds of the invention are suitable for the formation of photoresist coating compositions by admixture of at least one photoactive compound of formula I with a base-soluble matrix resin such as a novolak resin or a polyvinyl phenol resin form new photoresist compositions. Of particular utility are the positive-acting photoresists for forming relief micro-images and manufacture of novel articles from substrates coated with the new photoresist.

Lithographic properties such as photospeed and resolution of a light-sensitive photoresist composition comprising a naphthoquinone-diazide sulfonic acid ester and a matrix-resin are improved when at least one compound of formula I is incorporated into the photoresist composition.

As used herein, the term "photoresist" or "photoresist composition" is intended to include any photoimageable composition, although preferred aspects of the invention include use of high resolution photoresists, that is resists that can provide well resolved micron and submicron relief images, e.g., features of about 1.0 μm or less with essentially vertical sidewalls. As used herein, the term "activated radiation" refers to energy of a suitable dose and wavelength to provide a relief image when appropriately applied to a photoresist coating.

DETAILED DESCRIPTION OF THE INVENTION

The novel photoactive compositions of formula I are prepared from polyhydroxy polynuclear intermediates prepared by the synthetic route depicted in the Schemes below. Throughout the following discussion, the groups R through $R_4$ and X have the meaning given above.

Scheme

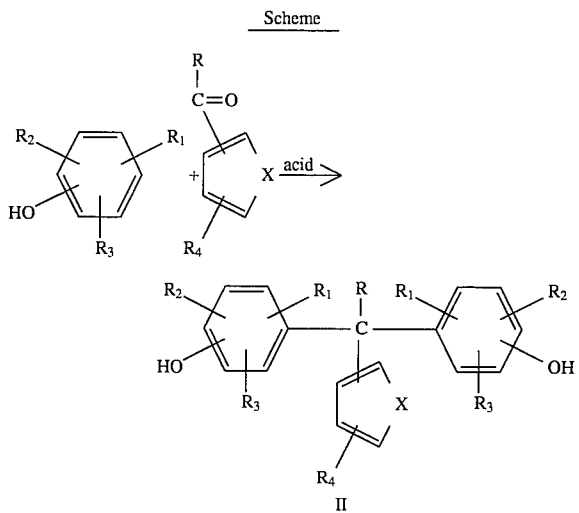

In accordance with the above Scheme, a molar excess of one or more phenols and the carbonyl compound are reacted in the presence of an acid catalyst and a suitable solvent to provide the polynuclear compound of formula II. The carbonyl compound may be a ketone group or an aldehyde group. Preferably the carbonyl group is an aldehyde. The phenolic reactant may be a mono-hydroxyl compound, a dihydroxyl compound or a trihydroxyl compound. Preferably the phenolic compound contains one hydroxyl or two hydroxyl groups.

The polynuclear compound of formula II may be prepared by reacting a phenol compound with a carbonyl compound of formula III:

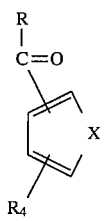

wherein R, $R_4$ and X are the same as defined above, in the presence of an acid catalyst.

A variety of phenols will be suitable for use in preparing compounds of formula I. As mentioned, generally preferred are the monohydroxyl and dihydroxyphenols. Examples of the monohydroxyl and dihydroxyphenols include phenol, o-cresol, m-cresol, p-cresol, 2,3 xylenol, 2,5-xylenol, 3,4-xylenol, 3,5-xylenol, 2,3,5-trimethylphenol, 2-tert-butylphenol, 3-tert-butyl-phenol, 4-tert-butylphenol, 2-tert-butyl-4-methylphenol, 2-tert-butyl-5-methylphenol, 2-methoxyphenol, 2,6-dimethoxyphenol, 3-methoxyphenol, 4-methoxyphenol, 2-ethylphenol, 3-ethylphenol, 4-ethylphenol, diethylphenol, triethylphenol, catechol, 3-methylcatechol, 3-methoxycatechol, 4-methylcatechol, resorcinol, 2-methylresorcinol, 4-methylresorcinol, 5-methylresorcinol, 4-ethylresorcinol, 4-hexylresorcinol, 5-pentylresorcinol, 2,5-dimethylresorcinol, 5-methoxyresorcinol, 4-chlororesorcinol, 4-bromoresorcinol and the like. Among them, monomethylphenols, dimethylphenols, trimethylphenol, methylresorcinol, ethylresorcinol, and hexylresorcinols are preferred.

In preferred aspects of the invention, the molar ratio of the phenol(s) to the carbonyl compound of at least 2:1 is employed. A larger relative amount of the phenol(s) can be employed if desired. Suitable solvents in which the reaction may be conducted include polar solvents such as alcoholic solvents, (e.g., methanol, ethanol, isopropanol, n-butanol, isoamyl alcohol, etc.), methyl isobutylketone, methyl ethylketone, ethylcellosolve acetate and so on. The condensation reaction may be conducted at below room temperature, at room temperature or at elevated temperatures. Preferably the reaction is conducted under conditions which minimize side reactions yet drive the reaction to completion at an acceptable rate. A reaction temperature is usually from 20° to 110° C. and a reaction time is from 30 minutes to 25 hours. The reaction may be conducted in the presence or absence of a solvent. The acid catalyst employed in the condensation reaction is used in a condensation reaction effective amount. Suitable acids for use in the reaction include inorganic acids (e.g. hydrochloric acid, sulfuric acid, etc.) and organic acids (e.g. oxalic acid, p-toluenesulfonic acid, etc.). After reaction completion, the product can be isolated by known means, for example by quenching the reaction solution into water and recovering the precipitated polynuclear compound.

The product may be further purified by washing it with a solvent or by recrystallization. Another method by which the product is purified is dissolving it in a water miscible solvent such as methanol, ethanol, acetone, and so on, and the solution charged into ion-exchanged water to precipitate the product. This method is preferred because the removal of catalyst and metal ions and purification of the condensation product are done at the same time.

Typically a mixture of polynuclear compounds is formed as a result of the condensation reaction, the predominant species being the compound depicted in the Scheme above. The present invention thus includes both substantially or essentially pure intermediate compounds of formula II as well as such compounds in mixture with other reaction products of the condensation reaction.

The photoactive compounds of formula I are prepared from the polyhydroxy polynuclear intermediates of formula II by their condensation with naphthoquinone diazide sulfonyl compounds. Any naphthoquinone diazide sulfonyl compound used in making photoresist sensitizers may be employed herein. The most preferred naphthoquinone diazo sulfonyl ester moieties are derived from 1,2-naphthoquinone-(2)-diazo-4-sulfonyl acid chloride or 1,2-naphthoquinone-(2)-diazo-5-sulfonyl acid chloride. These 4- and 5-sulfonyl ester groups respectively have the following formulae:

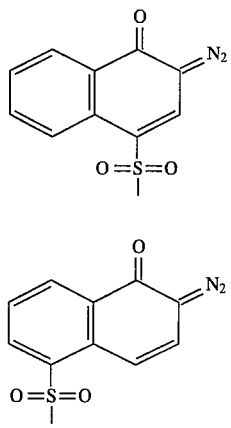

It is understood that the present invention includes the use of naphthoquinone diazide sulfonyl moieties singly or in mixtures in the condensation reaction with the compound of formula II. Also, the present invention includes separate, concurrent or sequential reactions of the polyhydroxy polynuclear compounds of formula II with different naphthoquinone diazide sulfonyl moieties. Furthermore the present invention encompasses phenolic ester mixtures formed by the condensation reaction of a naphthoquinone diazide sulfonyl chloride and another ester forming moiety with the compound of formula II. These other ester forming moieties may include methanesulfonyl chloride, ethanesulfonyl chloride, toluenesulfonyl chloride, acetyl halide, trimethylsilane chloride and the like.

The condensation reaction may be conducted under any conventional ester condensation conditions. Preferably, the ester compounds of formula I are prepared by first dissolving the compounds of formula II and the sulfonic acid chloride in a suitable solvent. Suitable solvents include acetone, dioxane, tetrahydrofuran, N-methylpyrrolidone, gamma-butyrolactone, ethyl lactate and the like. It is advantageous to carry out the condensation reaction in the presence of an acid-scavenging base, such as alkali metal carbonates, tertiary aliphatic amines, pyridine, pyridine derivatives, guanadine and guanadine derivatives. The organic bases are the most preferred for forming ester products free of alkali metals.

The esterification products of the reaction may be recovered from the reaction mixture by any conventional means. Preferably the reaction mixture is neutralized with an acid, the insoluble salts removed by filtration and the solution added to water. If desired, the filtered reaction mixture may be precipitated into acidified water. The precipitated product is collected by filtration, washed with water and dried. Suitable neutralization acids are hydrochloric acid, sulfuric acid, acetic acid, formic acid and the like.

At least one of the ester compounds of the present invention may be mixed with an alkali-soluble resin or resin mixtures and blends to make radiation sensitive mixtures which are useful as positive-working photoresist compositions. A preferred amount of the photoactive compound of formula I in a photoresist composition is from 4 to 40 parts by weight, preferably 6 to 30 parts by weight, per 100 parts by weight of the alkali-soluble resin. When the amount of the photoactive compound of formula I is in this range, a suitable photoresist pattern is produced. Other naphthoquinonediazide sulfonyl esters may be incorporated into the positive-acting photoresist compositions, if desired, in an amount of, for example, 30 parts by weight or less, preferably 20 parts by weight or less, per 100 parts by weight of the alkali-soluble resin. Exemplary naphthoquinonediazide compounds comprise naphthoquinone-(1,2)-diazide-(2)-4-sulfonyl and naphthoquinone-(1,2)-diazide-(2)-5-sulfonyl esters of pyrogallol alkyl ketone, pyrogallol aryl ketone, pyrogallol hydroxyaryl ketone, mono and dihydroxyaryl alkyl, mono and dihydroxyaryl alkyl ketone, mono and dihydroxyaryl ketone, 2,6-bis(4-hydroxy-3,5-dimethylbenzyl)-4-methylphenol, 2,6-bis(4-hydroxy-2,3,5-trimethylbenzyl)-4-methylphenol, 2,4-bis(4-hydroxy-3,5-dimethylbenzyl)-6-methylphenol, 2,4-bis(4-hydroxy-2,3,5-trimethylbenzyl)-6-methylphenol, 2,6-bis(2,4-dihydroxybenzyl)-4-methylphenol, bis(2,4-dihydroxy-3-methylbenzene)methylene, condensation products of salicylaldehyde and trimethylphenol, phenol aldehyde condensates, phenol ketone condensates, resorcinol acetone condensates, pyrogallol acetone condensate, alkylated phenol aldehyde condensate, novolak resins of alkylated phenol and aldehyde, alkylated phenol and formaldehyde, alkylated phenol and alkylaldehyde, alkylated phenol and aromatic aldehyde. Such blends of photoactive compounds can improve inhibition, coating properties, depth of focus, etch resistance, photospeed, resolution and feature profiles.

As the alkali-soluble resin for use of the compounds of the invention in a photoresist formulation, any of the alkali-soluble resins which are used in the positive photoresist composition may be used. Preferred examples of the alkali-soluble resins are the hydroxy aryl-based resins such as novolak, modified novolak, polyvinylphenol, copolymers of polyvinylphenols and so on. One class of preferred novolak resin is prepared by an addition condensation reaction of a phenol compound with an aldehyde. Specific examples of the phenol compound used as a reactant in the condensation reaction include phenol o-cresol, m-cresol, p-cresol, 2-ethylphenol, 3-ethylphenol, 4-ethylphenol, 2,3-dimethylphenol, 2,5-dimethylphenol, 3,5-dimethylphenol, 3,6-dimethylphenol, 3,4-dimethylphenol, 2,3,5-trimethylphenol, 2-sec-butylphenol, 3-sec-butylphenol, 4-sec-butylphenol, 2-tert-butylphenol, 3-tert-butylphenol, 4-tert-butylphenol, 2-tert-butyl-4-methylphenol, 2-tert-butyl-5-methylphenol, 2-tert-butyl-6-methylphenol, resorcinol, 2-methylresorcinol, 4-ethylresorcinol, catechol, naphthol, dihydroxynaphthalene, etc. These phenols may be used alone or in combination.

The above condensation reaction used to form the alkali soluble resin may be conducted in the presence or absence of a solvent. Usually the reaction is carried out at about 60° to 145° C. for about 2 to 36 hours. Examples of aldehyde that may be used are formaldehyde, paraformaldehyde, acetaldehyde, benzaldehyde, salicylaldehyde, furfural and the like. The aldehyde may be used alone, as an admixture of different aldehydes added sequentially. Examples of catalysts used in the condensation reaction include organic and inorganic acids (e.g. oxalic acid, hydrochloric acid, sulfuric acid, perchloric acid, benzenesulfonic acid, toluenesulfonic acid, methanesulfonic acid, trifluoroacetic acid, trichloroacetic acid, formic acid, phosphoric acid, etc.) and divalent inorganic metal salts of zinc, magnesium, manganese, nickel, copper, cobalt and the like. The organic and mineral acid catalysts may be used alone or as mixtures. If desired, divalent sulfur co-catalysts may be also used.

Other useful alkali-soluble resins that can be used with the radiation-sensitive composition are disclosed in U.S. Pat. Nos. 5,216,111 and 5,238,776, each incorporated herein by reference. In accordance with the procedures set forth in U.S. Pat. No. 5,238,776, a first aromatic aldehyde resin is formed by the condensation of a bis-hydroxymethylated phenol with another reactive phenol in the absence of an aldehyde to form an alternating novolak copolymer. In accordance with the procedures of U.S. Pat. No. 5,216,111, a phenol is reacted with an aromatic aldehyde to produce a novolak resin. The aromatic novolak resins produced by either patent can then be chain extended to increase molecular weight and thermal properties by further reaction with an aldehyde which may be aliphatic or aromatic aldehyde to form a block copolymer; or by the reaction with an aldehyde which may be an aliphatic or aromatic aldehyde with another phenol to form a block copolymer; or by the reaction with a bishydroxymethylated phenol alone or in combination with an additional reactive phenol.

Two or more resins of similar or different compositions can be blended or combined together to give improved control of lithographic properties of positive photoresist compositions. Useful alkali-soluble resin blend compositions are disclosed in U.S. Pat. No. 5,266,440, incorporated herein by reference.

A positive photoresist composition is prepared using the photoactive compounds of the invention by mixing and dissolving the components in a suitable photoresist solvent. Known photoresist solvents include, for example, ether esters such as ethyl cellosolve acetate, methyl cellosolve acetate, and propylene glycol monomethyl ether acetate; carboxylates such as ethyl acetate and butyl acetate; lactones such as butyrolactone; ketones such as cyclohexanone and 2-heptanone; carboxylates of dibasic acids such as diethyloxylate and diethylmalonate; dicarboxylates of glycols such as ethylene glycol diacetate and propylene glycol diacetate; hydroxy carboxylates such as ethyl-2-hydroxypropionate (ethyl lactate), ethyl 2-hydroxyisobutyrate and ethyl-3-hydroxypropionate; carboxylates such as amyl and isoamyl acetate; and aromatic ethers such as anisole and methyl anisole. Solvents may be used alone or in admixture with each other and may be further mixed with non-solvents for one or more of the constituents. Suitable photoresist coating compositions can contain up to 50 percent by weight solids and preferably from 20 to 40 percent solids.

Other additives that may be added to the photoresist coating composition include actinic and contrast dyes, antistriation agents, plasticizers, speed enhancers and the like as would be known to those skilled in the art.

The method of using the photoresist of the invention is in accordance with prior art procedures. The most conventional methods comprise forming a film from a solution by whirl coating, dipping, spraying, etc. The photoresists compositions may also be applied as a dry film in accordance with the art recognized procedures.

The photoresist compositions of this invention are applied to conventional substrates and conventional manners. For example, the photoresist may be applied to a copper clad substrate, a semiconducter, a silicon wafer, etc. by any whirl coating, spraying, dipping or the like. Thereafter, the substrate is dried, imaged and developed by washing with an aqueous alkaline developer.

The present invention is further described in detail by means of the following Examples.

EXAMPLE 1

Preparation of α,α'-bis(2,4-dihydroxy-4-ethyl)phenyl-2-methylthiophene

Into a 500 mL round bottom flask equipped with a magnetic stirrer and a stopper, 4-ethylresorcinol (74.6 g), 2-thiophenecarboxaldehyde (30.2 g), methanol (300 mL) and concentrated hydrochloric acid (0.3 g) were charged and reacted for about 18 hours at ambient temperature while stirring. Then, the mixture was added dropwise into 3000 mL of de-ionized water while vigorously stirred to precipitate the product. The product was filtered, washed with de-ionized water and dried at about 85° C. under vacuum to give 95.5 g (95.5% of theory) of a compound represented by the following formula. High pressure liquid chromatography, HPLC, (flow rate was 1.8 mL/min.; eluant mixture comprised of 27% tetrahydrofuran and 73% isooctane; using a 15 cm 3μ CN column with detection at 254 nm) exhibited a purity of 95.8%. Recrystallization from a 60% de-ionized water-40% dioxane mixture increased the product purity to 97.7%. Melting point: 212° C.

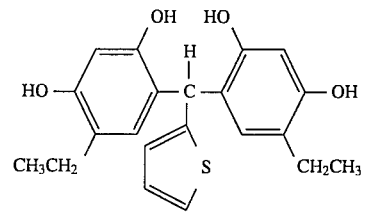

$^{13}$NMR (in acetone-$d_6$, ppm from TMS):14.40 (—CH$_3$), 22.56 (—CH$_2$—), 36.99 (triarylmethane methine), 102.45 (aromatic C-2), 120.94 (aromatic C-6), 121.86 (aromatic C-4), 123.43 (thiophene C-5), 125.32 (thiophene C-3), 126.09 (thiophene C-4), 129.92 (aromatic C-5), 150.08 (thiophene C-2), 152.87 (aromatic C-1), 153.74 (aromatic C-3).

EXAMPLE 2

Esterification of the Product of Example 1 with 3.7 Moles of 1,2-naphthoquinone-(2)-diazo-5-sulfonyl Acid Chloride Into a 2 L three-necked round bottom flask fitted with a stirrer, constant temperature water bath, pressure equalizing addition funnel, and thermometer was added 40.0 g (108.1 mmol) of α,α'-bis(2,4-dihydroxy-4-ethyl)phenyl-2-methylthiophene, 107.4 g (400 mmol) of 1,2-naphthoquinone-(2)-diazo-5-sulfonyl acid chloride and 900 mL acetone. The stirring was begun and after all reactants had dissolved and the mixture equilibrated at about 30° C., a solution of triethylamine (48.5 g, 480.2 mmol) and acetone (100 mL) was added over 20 minutes. The stirring was continued for 1.5 hours while the reaction mixture was kept at 30° C.

The reaction mixture was filtered to remove the hydrochloride salt, 9 mL of water added and the solution stirred for 30 minutes. The reaction mixture was neutralized with concentrated hydrochloric acid and then added into 9 L of de-ionized water to precipitate the product. The product was collected on a filter, rinsed with water and dried at 45° C.

under vacuum. About 127.1 g (95% of theory) of product was obtained.

HPLC assay (3 m CN column, 15 cm length, 30%/70% tetrahydrofuran/isooctane eluant mixture at 2.1 mL/min flow rate, detection at 254 nm) showed the product ester mixture to comprise (area percent) about 7.4% diester, about 5% triester and about 86.9% tetraester.

To test the above ester mixture solution stability in a typical resist solvent, 5% by weight solutions were prepared using a solvent mixture comprising of 80% ethyl lactate, 13% anisole and 7% amyl acetate. For the first two weeks of the test the solutions were checked visually and under an optical microscope for particles, then they were checked biweekly. These tests were conducted both at ambient an at 40° C. The solution stability of the ester mixture was more than 850 hours at 40° C. and more than 2100 hours at ambient temperature.

EXAMPLE 3

Esterification of Product of Example 1 with 1,2-naphthoquinone-(2) diazo-4-sulfonic Acid Chloride Under similar reaction conditions as in Example 2, the 1,2-naphthoquinone-(2)-diazo-4-sulfonic acid mixed esters of α,α'-bis(2,4-dihydroxy-4-ethyl)phenyl-2-methylthiophene were prepared in 84.3% yield. HPLC assay data was indicative of about 13% diester, about 2.1% combined triesters and about 83.6% tetraester.

EXAMPLE 4

Esterification of Product of Example 1 with a Sulfonic Acid Chloride Mixture

Using the procedure set fourth in Example 2 a 1:1 mixture of 1,2-naphthoquinone-(2)-diazo-4-sulfonyl chloride and 1,2-naphthoquinone-(2)-diazo-5-sulfonyl chloride were reacted with α,α'-bis(2,4-dihydroxy-4-ethyl)phenyl-2-methylthiophene to produce an ester mixture in about 97.9% yield.

EXAMPLE 5

Preparation of α,α'-bis(2,4-dihydroxy-4-ethyl)phenyl-2-methyl-5-methylfuran

Into a 250 mL round bottom flask equipped with a magnetic stirrer and a stopper, 4-ethylresorcinol (30.0 g), 5-methyl-2-furancarboxaldehyde (11.96 g), methanol (120 mL) and concentrated hydrochloric acid (0.1 g) were charged and reacted for about 45 minutes at ambient temperature while stirring. Then, the mixture was added dropwise into 1200 mL of de-ionized water while vigorously stirred to precipitate the product. The product was filtered, washed with de-ionized water and dried at about 85° C. under vacuum to give 30 g (75% of theory) of a compound represented by the following formula. HPLC exhibited a purity of 96.4%. Recrystallization from a 66% de-ionized water-34% dioxane mixture resulted in a pure compound. Melting point: 150° C.

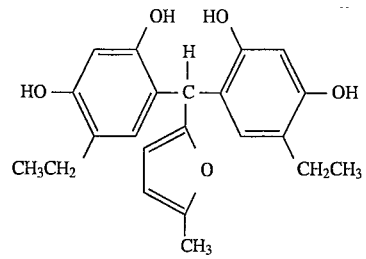

$^1$H NMR (acetone-$d_6$, ppm from TMS): 8.0–7.8 (d, 4H), 6.75 (s, 2H), 6.4 (s, 2H), 6.0–5.6 (m, 3H), 2.6–2.0 (m, 7H), 1.05 (t, 6H). $^{13}$C NMR (in acetone-$d_6$, ppm from TMS): 12.69 (furan C-5 methyl), 14.28 (—CH$_3$), 22.46 (—CH$_2$—), 36.06 (triarylmethane methine), 102.43 (aromatic C-2), 105.61 (furan C-3), 107.96 (furan C-4), 119.87 (aromatic C-6), 120.95 (aromatic C-4), 129.74 (aromatic C-5), 150.03 (furan C-5), 152.82 (aromatic C-1), 153.62 (aromatic C-3), 156.28 (furan C-2).

EXAMPLE 6

Esterification of Product of Example 5

Under analogous reaction conditions of Example 2, 3.7 parts of 1,2-naphthoquinone-(2)-diazo-5-sulfonyl chloride were condensed with 1 part of α,α'-bis(2,4-dihydroxy-4-ethyl)phenyl-2-methyl-5-methylfuran to produce the mixed ester in about 97% yield. HPLC assay (analytical conditions as described in Example 2) showed about 7.1% diester, about 4.1% total triester and about 86.8% tetraester.

The solution stability of the above ester mixture was determined analogous to Example 2. The ester mixture was found to stay soluble for over 2100 hours at ambient temperature and over 850 hours at 45° C.

EXAMPLE 7

Preparation of α,α'-Bis(2,4-dihydroxy-3-methyl)-2-methylthiophene

Into a 100 mL round bottom flask equipped with a magnetic stirrer and a stopper, 2-methylresorcinol (7.25 g), 2-thiophene-carboxaldehyde (3.27 g), methanol (30 mL) and concentrated hydrochloric acid (0.3 g) were charged and reacted for about 75 minutes at ambient temperature while stirring. HPLC analysis showed the reaction mixture to comprise of 33% of α,α'-bis(2,4-dihydroxy-3-methyl)phenyl-2-methylthiophene, 30% of dimers and 35% of oligomers.

EXAMPLE 8

Preparation of α,α'-Bis(4-hydroxy-2,5-dimethyl)phenyl-2-methylthiophene

Into a 100 mL round bottom flask equipped with a magnetic stirrer and reflux condenser, 2,5-xylenol (7.22 g), 2-thiophene-carboxaldehyde (3.31 g), methanol (30 mL) and concentrated hydrochloric acid (3mL) were charged and reacted at reflux for 5 hours while stirring. Then, the mixture was added dropwise into 1000 mL of de-ionized water while vigorously stirred to precipitate the product. The product was filtered, washed with de-ionized water and dried at about 95° C. under vacuum to give 9.1 g (91% of theory) of a compound represented by the following formula. HPLC exhibited a purity of 89.7%.

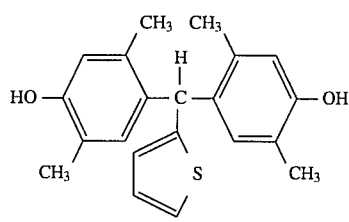

$^{13}$C NMR (acetone-d$_6$, ppm from TMS): 15.15 (aromatic C-2 methyl), 18.24 (aromatic C-5 methyl), 43.67 (triarylmethane methine), 116.60 (aromatic C-6), 120.73 (aromatic C-4), 124.07 (thiophene C-5), 126.10 (thiophene C-3), 126.32 (thiophene C-4), 130.58 (aromatic C-3), 133.25 (aromatic C-2), 134.24 (aromatic C-5), 148.53 (thiophene C-2), 153.58 (aromatic C-1).

EXAMPLE 9

Preparation of α,α'-Bis(4-hydroxy-2,3,6-trimethyl)phenyl-2-methylthiophene

Under similar reaction conditions as in EXAMPLE 4, α,α'-bis(4-hydroxy-2,3,6-trimethyl)phenyl-2-methylthiophene was prepared with a purity of 88.9%

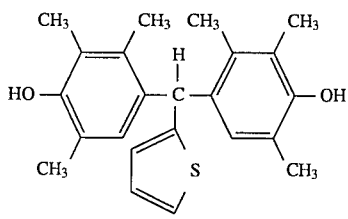

$^{13}$C NMR (acetone-d$_6$, ppm from TMS): 12.00 (aromatic C-2 methyl), 14.57 (aromatic C-6 methyl), 16.12 (aromatic C-3 methyl), 45.08 (triarylmethane methine), 120.22 (aromatic C-6), 122.90 (aromatic C-2), 124.03 (thiophene C-5), 126.28 (thiophene C-3), 128.00 (aromatic C-5), 132.85 (aromatic C-4), 133.85 (aromatic C-3), 149.14 (thiophene C-2), 151.40 (aromatic C-1).

EXAMPLE 10

Preparation of α,α'-bis(2,4-dihydroxy-3-methyl)phenyl-2-methyl-5-bromothiophene Using the reaction conditions set forth in Example 8, α,α'-bis(2,4-dihydroxy-3-methyl)phenyl-2-methyl-5-bromothiophene was prepared.

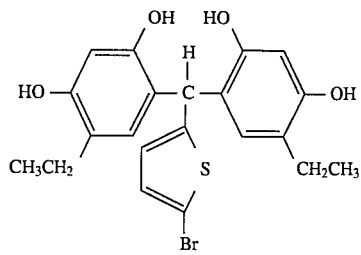

EXAMPLE 11

Light Sensitive Composition

A resist formulation consisting of 2.42 g of the photosensitive esters of Example 2, 11.68 g of 2,5-xylenol/bismethylol-p-cresol (60/40) novolak resin, and 44.21 g of a solvent mixture comprising of 80% ethyl lactate, 13% anisole, and 7% amylacetate was filtered through a 0.2 micron filter, spin cast to 0.9 micron film on a 4 inch silicon wafer, prebaked at 90° C. for 1 min., exposed at 214 mJ/cm$^2$ on a GCA AL200 0.55NA I-line stepper, post expose baked at 115° C. for 1 min., developed in 0.24N TMAH, and examined by electron microscopy. Straight walled profiles were observed for images down to 0.35 microns. This along with the solubility data demonstrates the superior performance of the naphthoquinone diazide esters of the invention.

EXAMPLE 12

Light Sensitive Composition with α,α'-Bis(2,4-dihydroxy-4-ethyl)phenyl-2-methylthiophene as Speed Enhancer A resist formulation consisting of 2.42 g of the photosensitive esters of Example 2, 10.51 g of 2.5-Xylenol/bismethylol-p-cresol (60/40) novolak resin, 1.17 g of compound of Example 1, and 44.21 g of a solvent mixture comprising of 80% ethyl lactate, 13% anisole, and 7% amylacetate, was spin cast to 0.97 micron film on a 4 inch silicon wafer, prebaked at 90° C. for 1 min., exposed at 136 mJ/cm$^2$ on a GCA AL200 0.55NA I-line stepper, post expose baked at 115° C. for 1 min., developed in 0.24N TMAH, and examined by electron microscopy. Images with good wall profiles were resolved down to 0.45 microns.

We claim:

1. A compound corresponding to the formula:

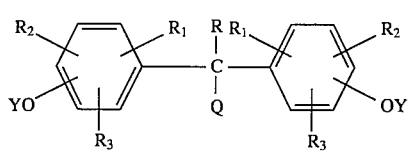

I whereby each Y is independently selected from the group consisting of hydrogen, lower alkyl having from 1 to 5 carbon atoms, R'SO$_2$, acyl, (R')$_3$Si and a naphthoquinone diazide sulfonyl group where each R' is independently selected from the group of lower alkyl having from 1 to 5 carbon atoms and aryl provided that at least one Y is a naphthoquinone diazide sulfonyl group; R is a member selected from the group consisting of hydrogen, lower alkyl having from 1 to 5 carbon atoms, cyclic alkyl, and aryl; R$_1$, R$_2$ and R$_3$ are each independently selected form the group consisting of hydrogen, hydroxyl, lower alkyl having from 1 to 5 carbon atoms, cyclic alkyl, aryl, alkoxy, alkenyl, alkynyl, nitro, alkanoyl, carboxyl, sulfonyl and halogen; and Q is a five member heterocyclic group.

2. The compound of claim 1 where the heterocyclic group contains a member selected from the group consisting of oxygen, sulfur and nitrogen in the heterocyclic ring.

3. The compound of claim 1 where the heterocyclic group contains sulfur in the heterocyclic group.

4. The compound of claim 1 where the heterocyclic group contains oxygen in the heterocyclic ring.

5. The compound of claim 1 where one of said Ys is hydrogen.

6. The compound claim 1 where each Y is a naphthoquinone diazide sulfonyl group.

7. The compound of claim 1 where at least one of $R_1$, $R_2$ or $R_3$ is hydroxyl.

8. A compound corresponding to the formula:

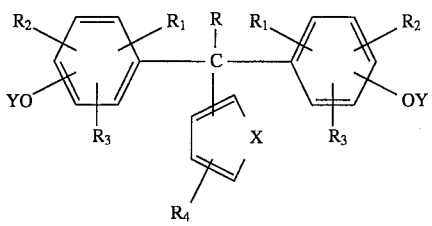

where each Y is independently selected from the group consisting of hydrogen, lower alkyl having from 1 to 5 carbon atoms, R'SO$_2$, acyl, (R')$_3$Si and a naphthoquinone diazide sulfonyl group where each R' is independently selected from the group of lower alkyl having from 1 to 5 carbon atoms and aryl provided that at least one Y is a naphthoquinone diazide sulfonyl group; X is a member selected for the group consisting of oxygen and sulfur; R is a member selected from the group consisting of hydrogen, lower alkyl having from 1 to 5 carbon atoms, cyclic alkyl, aryl and a heterocyclic; and $R_1$, $R_2$ and $R_3$ are each independently selected form the group consisting of hydrogen, hydroxyl, lower alkyl having from 1 to 5 carbon atoms, cyclic alkyl, aryl, alkoxy, alkenyl, alkynyl, nitro, alkanoyl, carboxyl, sulfonyl and halogen; and $R_4$ is selected from the group consisting of hydrogen, lower alkyl having from 1 to 5 carbon atoms, alkoxy, alkenyl, alkynyl, carboxyl, alkoxy, carbonyl, nitro and halogen.

9. The compound of claim 8 where each Y is a naphthoquinone diazide sulfonyl group.

10. The compound of claim 8 where at least one of $R_1$, $R_2$ or $R_3$ is hydroxyl.

11. A method for formation of a diazo ester, said method comprising the reaction of a molar excess of a phenol with a carbonyl in the presence of an acid catalyst in accordance with the following scheme:

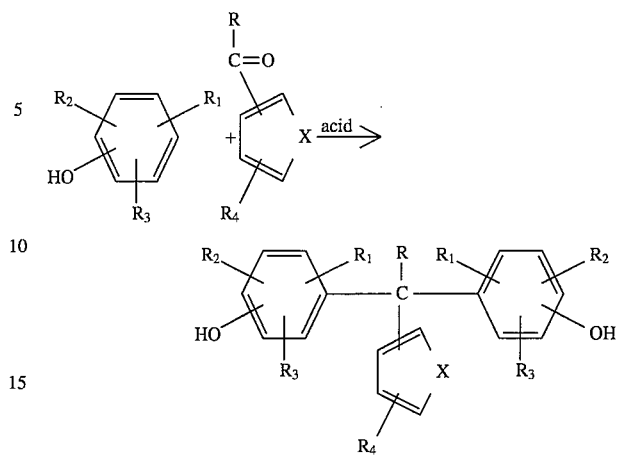

where X is a member selected for the group consisting of oxygen and sulfur; R is a member selected from the group consisting of hydrogen, lower alkyl having from 1 to 5 carbon atoms, cyclic alkyl, and aryl; and $R_1$, $R_2$ and $R_3$ are each independently selected form the group consisting of hydrogen, hydroxyl, lower alkyl having from 1 to 5 carbon atoms, cyclic alkyl, aryl, alkoxy, alkenyl, alkynyl, nitro, alkanoyl, carboxyl, sulfonyl and halogen; and $R_4$ is selected from the group consisting of hydrogen, lower alkyl having from 1 to 5 carbon atoms, alkoxy, alkenyl, alkynyl, carboxyl, alkoxy, carbonyl, nitro and halogen and reacting the compound thus formed with a naphthoquinone diazide sulfonyl chloride.

12. The method of claim 1 where the acid is a mineral acid.

13. The method of claim 11 where there are at least two moles of the phenol per mole of the carbonyl compound.

14. The method of claim 11 where the napthoquinone diazide sulfonyl chloride is a 1,2-naphthoquiunone-(2)-diazo-4-sulfonyl acid chloride.

15. The method of claim 11 where the naphthoquinone diazide sulfonyl chloride is a 1,2-naphthoquinoe diazide-(2)-diazo-5-sulfonyl acid chloride.

* * * * *